United States Patent [19]

Toth et al.

[11] Patent Number: 5,224,136

[45] Date of Patent: Jun. 29, 1993

[54] HELICAL SCANNING COMPUTED TOMOGRAPHY APPARATUS WITH CONSTRAINED TRACKING OF THE X-RAY SOURCE

[75] Inventors: Thomas L. Toth, Brookfield; Kevin F. King, New Berlin; Carl R. Crawford, Milwaukee, all of Wis.

[73] Assignee: General Electric Company, Milwaukee, Wis.

[21] Appl. No.: 906,805

[22] Filed: Jun. 30, 1992

[51] Int. Cl.⁵ .............................................. G21K 1/04
[52] U.S. Cl. .............................................. 378/4; 378/14; 378/146
[58] Field of Search .................... 378/4, 11, 14, 15, 17, 378/19, 20, 22, 25, 145, 146, 147, 149, 137

[56] References Cited

U.S. PATENT DOCUMENTS

| | | | |
|---|---|---|---|
| 4,277,685 | 7/1981 | Covic et al. | 250/445 |
| 4,426,715 | 1/1984 | Baer et al. | 378/4 |
| 4,630,202 | 12/1986 | Mori | 364/414 |
| 4,789,929 | 12/1988 | Nishimura et al. | 364/413.15 |
| 4,972,458 | 11/1990 | Plewes | 378/146 |
| 4,991,189 | 2/1991 | Boomgaarden et al. | 378/4 |
| 5,046,003 | 9/1991 | Crawford | 378/15 |
| 5,073,911 | 12/1991 | Ozaki et al. | 378/17 |
| 5,090,037 | 2/1992 | Toth et al. | 378/4 |
| 5,170,346 | 12/1992 | Crawford et al. | 378/14 |

Primary Examiner—David P. Porta
Attorney, Agent, or Firm—Quarles & Brady

[57] ABSTRACT

A CT apparatus reduces errors in projection data acquired in helical scanning. The imaged object moves concurrently along a translation axis and the x-ray beam is periodically translated with the imaged object so as to subtend a single predetermined volume element during the acquisition of one projection set of data for a first slice. The x-ray beam then returns to its starting position and tracks a second predetermined volume element within a next slice. The x-ray beam may be translated by moving the focal point or a collimator or a combination of both. Helical scans with a pitch requiring sweeping of the x-ray beam beyond the detector limits are accommodated by limiting the sweep to a lessor compliance distance. The angular rate of the sweep is held constant within this compliance distance during the sweep.

8 Claims, 10 Drawing Sheets

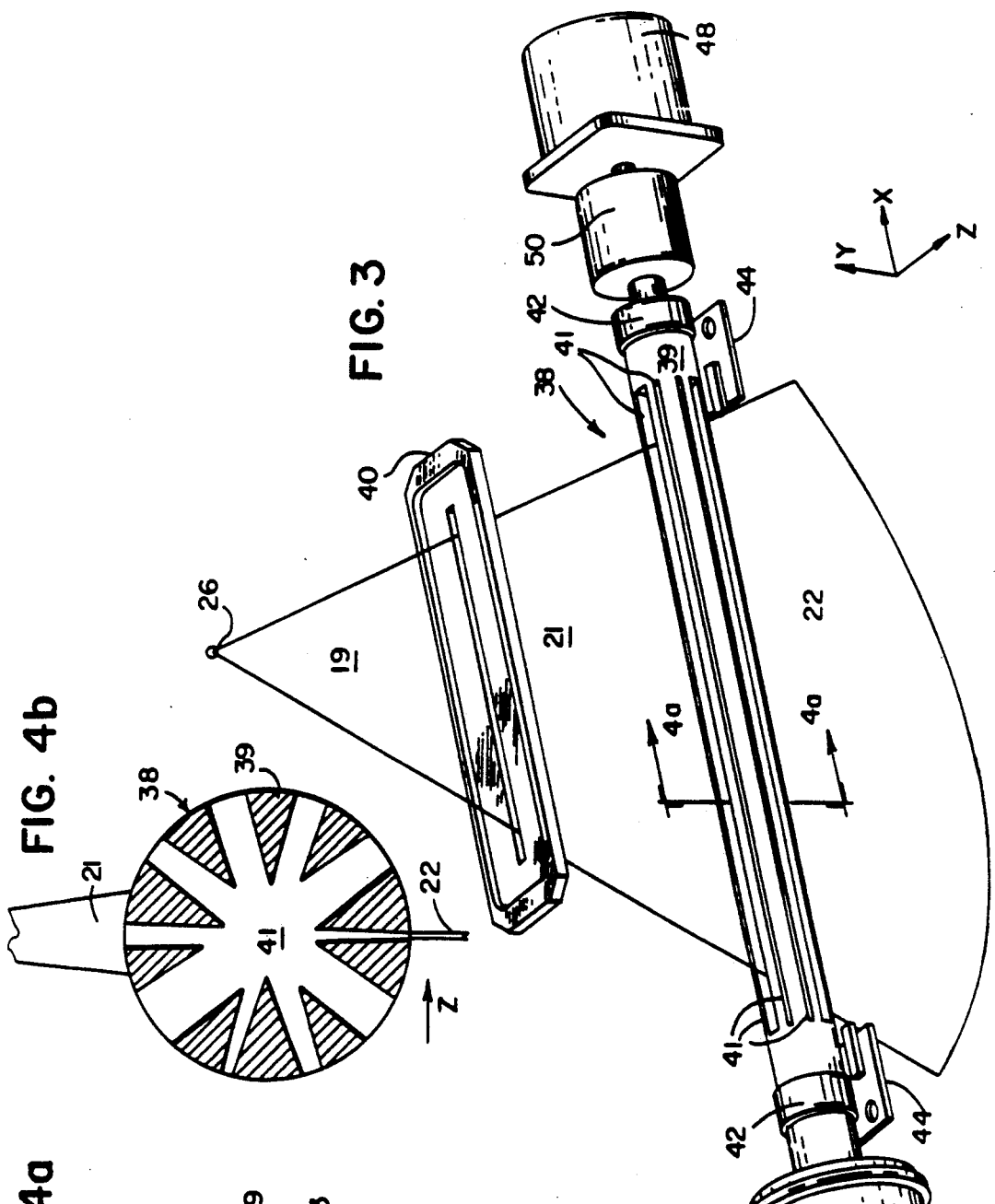
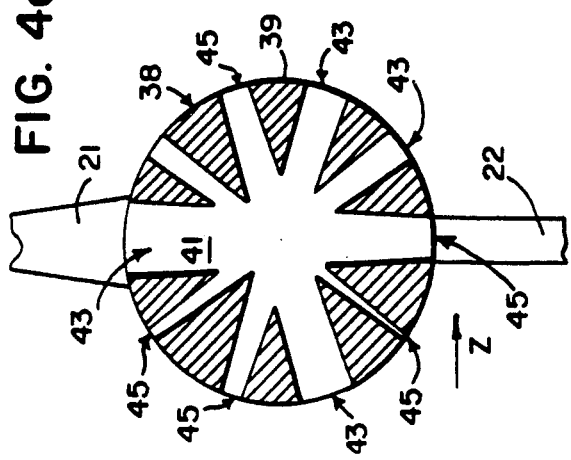

HELICAL SCANNING COMPUTED TOMOGRAPHY APPARATUS WITH CONSTRAINED TRACKING OF THE X-RAY SOURCE

BACKGROUND OF THE INVENTION

This invention relates to computed tomography (CT) systems and specifically to a helical scanning CT system in which the imaged object is concurrently translated during the acquisition of tomographic projections.

In a computed tomography system, an x-ray source is collimated to form a fan beam with a defined fan beam angle. The fan beam is typically oriented to lie within the x-y plane of a Cartesian coordinate system, termed the "gantry plane", and is transmitted through an imaged object to an x-ray detector array oriented within the gantry plane. The detector array is comprised of an array of detector elements each of which measures the intensity of transmitted radiation along a ray projected from the x-ray source to the particular detector element. The intensity of the transmitted radiation is dependent on the attenuation of the x-ray beam along that ray by the imaged object.

The center of the fan beam and its direction of the fan beam is identified by a fan beam axis.

The x-ray source and detector array may be rotated on a gantry within the gantry plane and around a center of rotation within the imaged object so that the angle at which the fan beam axis intersects the imaged object may be changed. At each gantry angle, a projection is acquired comprised of the intensity signals from each detector element. The gantry is then rotated to a new angle and the process is repeated to collect a number of projections along a number of gantry angles to form a tomographic projection set.

The acquired tomographic projection sets are typically stored in numerical form for later computer processing to "reconstruct" a slice image according to reconstruction algorithms known in the art. A projection set of fan beam projections may be reconstructed directly into an image by means of fan beam reconstruction techniques, or the intensity data of the projections may be sorted into parallel beams and reconstructed according to parallel beam reconstruction techniques. The reconstructed tomographic images may be displayed on a conventional CRT tube or may be converted to a film record by means of a computer controlled camera.

A typical computed tomographic study involves the acquisition of a series of "slices" of an imaged object, each slice parallel to the gantry plane and having a slice thickness dictated by the width of the detector array, the size of the focal spot, the collimation and the geometry of the system. Each successive slice is displaced incrementally along a z-axis, perpendicular to the x and y axes, so as to provide a third spatial dimension of information. A radiologist may visualize this third dimension by viewing the slice images in order of position along the z-axis, or the numerical data comprising the set of reconstructed slices may be compiled by computer programs to produce shaded, perspective representations of the imaged object in three dimensions.

As the resolving power of computed tomography methods increases, additional slices are required in the z-dimension. The time and expense of a tomographic study increases with the number of slices required. Also, the longer scan times necessary to acquire more slices increases the discomfort to the patient who must remain nearly motionless to preserve the fidelity of the tomographic reconstructions. Accordingly, there is considerable interest in reducing the time required to obtain a slice series.

The time required to collect the data for a series of slices depends in part on four components: a) the time required to accelerate the gantry to scanning speed, b) the time required to obtain a complete tomographic projection set, c) the time required to decelerate the gantry, and d) the time required to reposition the patient in the z-axis for the next slice. Reducing the time required to obtain a full slice series may be accomplished by reducing the time required to complete any of these four steps.

The time required for acceleration and deceleration of the gantry (a and c) may be avoided in tomographic systems that use slip rings rather than cables to communicate with the gantry. The slip rings permit continuous rotation of the gantry and avoid the need for acceleration and deceleration. Hereafter, it will be assumed that the CT systems discussed are equipped with slip rings or the equivalent to permit continuous rotation.

The time required to acquire the tomographic data set (b) is more difficult to reduce. Present CT scanners require on the order of one to two seconds to acquire the projection set for one slice. This scan time may be reduced by rotating the gantry at a faster speed. However, a higher gantry speed, in general, will decrease the signal-to-noise ratio of the acquired data by the square root of the factor of rotational rate increase. This may be overcome to some extent by increasing the radiation output of the x-ray tube, but is subject to the power limits of such devices.

Finally, a reduction in patient repositioning time (d) may be accomplished by translating the patient in the z-axis concurrently with the rotation of the gantry. The combination of continuous patient translation along the z-axis during the rotation of the gantry and acquisition of projection data has been termed "helical scanning" and refers to the apparent path of a point on the gantry with respect to a reference point on the imaged body. As used herein, "helical scanning" shall refer generally to the use of continuous translation of the patient or imaged object during the acquisition of tomographic imaging data, and "constant z-axis scanning" shall refer to the acquisition of the tomographic data set without translation of the patient or imaged object during the acquisition period.

Continuous translation of the imaged object during scanning shortens the total scanning time required for the acquisition of a given number of slices by eliminating the length of time normally required for repositioning the patient between scans. However, helical scanning introduces certain errors in the acquired tomographic projection sets. The mathematics of tomographic reconstruction assumes that the tomographic projection set is acquired along a constant z-axis slice plane. The helical scan path clearly deviates from this condition and this deviation results in image artifacts in the reconstructed slice image if there is any significant change in the object in the z-axis. The severity of the image artifacts depends generally on the "helix offset" in the projection data, measured as the z-axis difference between the scanned volume elements of the imaged object and the z axis value of the desired slice plane.

Errors resulting from helical scanning will be referred to collectively as "skew" errors.

Several methods have been used to reduce skew errors in helical scanning A first approach disclosed in U.S. Pat. No. 4,630,202 issued Dec. 16, 1986, reduces the pitch of the helical scan and then averages the projection data of consecutive 360° tomographic projection sets. The effect is equivalent to using a detector array with a larger width along the z axis, which also moves less in the z direction during a rotation of the gantry, i.e. with a lesser scanning pitch. Skew errors are reduced using this method, but at the expense of additional scanning time necessitated by the lower scanning pitch. Thus, this method reduces, to some extent, the advantages to be gained by helical scanning.

Skew errors at the ends of the tomographic projection set may be reduced in conjunction with this approach by changing the weighting of the last and first projections of the consecutive 360° tomographic projection sets in the "averaging" process to give greater weight to the projection closest to the slice plane.

A second approach disclosed in U.S. Pat. No. 4,789,929 issued Dec. 6, 1988, also applies weighting to the projections of combined, consecutive 360° tomographic projection sets, but the weighting is a function of the helix offset of each projection at the given gantry angle. This approach of interpolating over 720° generally increases partial volume artifacts. Partial volume artifacts are image artifacts arising when certain volume elements of the imaged object contribute to only some of the projections of the projection set.

A third approach, described in co-pending U.S. patent application Ser. No. 07/435,980, entitled: "Extrapolative Reconstruction Method for Helical Scanning" and assigned to the same assignee as the present invention, uses a half-scanning technique to reduce the table motion during the acquisition of each slice. Projection data is acquired over 360° of gantry rotation and interpolated to a slice plane. The reduced gantry motion corresponds to reduced table motion and hence certain helical scanning artifacts are reduced.

In U.S. Pat. No. 5,090,037 entitled: "Helical Scanning Computed Tomography with Tracking X-ray Source", assigned to the same assignee as the present invention, skew error is reduced by translating the x-ray beam with translation of the imaged object. This translation may be accomplished by, for example, a movable collimator which sweeps the angle of the fan beam to track a particular volume element of the imaged object. Although this technique is successful in reducing the effects of helix offset, it has previously been assumed that it cannot be used for sequences of thick slices where there is the possibility that the edges of the fan beam will move beyond the edge of the detector.

SUMMARY OF THE INVENTION

The present invention allows the above described of sweeping the x-ray beam with the translation of the imaged object, to be extended to the imaging of thick slices. The invention generally recognizes that sweeping the fan beam can still reduce skew artifacts even if the sweeping is restrained to the width of a detector and cannot track a given volume element of a thick slice for the entire projection set.

Thus, in a first embodiment, for the imaging of thicker slices, the motion of the fan beam is simply stopped at the end of a compliance distance, as determined by the width of the detector, despite the greater motion of the imaged object. In a further embodiment, the position of the fan beam is held within the compliance distance and the sweeping motion is made to be of substantially constant velocity. This second embodiment recognizes that continuous angular motion of the fan beam is more important than actual tracking of a given volume element within the imaged object as previously thought.

Specifically, the present invention includes an x-ray generator for projecting a beam of x-rays through the imaged object to be received by an x-ray detector. Both the generator and detector are supported on a gantry for rotating the x-ray generator and x-ray detector about the imaged object in an gantry plane substantially perpendicular to a translation axis. A table supports and translates the imaged object by a translation distance along a translation axis with the acquisition of the projection set during a first period. The translation is concurrent with the rotation of the gantry per helical scanning.

A sweeping mechanism moves the x-ray beam by a predetermined compliance distance along the translation axis in a first direction during the first period, and in a second direction along the translation axis but counter to the translation of the imaged object during a second period. The compliance distance is limited to less than the translation distance. The beam of x-rays is received by the x-ray detector throughout the sweeping of the beam by the compliance distance.

It is one object of the invention to permit the sweeping of the fan beam in helical imaging of a series of thick slices to reduced skew error.

In one embodiment, the beam is centered on a predetermined volume element of the imaged object on the translation axis within the predetermined compliance distance during a first portion of the first period and stops sweeping during a second portion of the first period at the limit of the predetermined compliance distance.

In another embodiment, the x-ray beam is swept within the compliance distance so as to maintain a constant angular motion of the beam during the first period.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

BRIEF DESCRIPTION OF THE DRAWINGS

FIG. 3 is a perspective view of the collimator assembly of the present invention;

FIG. 4 (a) and (b) are cross-sectional views of the mandrel of the collimator of FIG. 3 showing orientation of the mandrel for thick and thin fan beams respectively;

DETAILED DESCRIPTION OF THE PREFERRED EMBODIMENT

Figure 1:
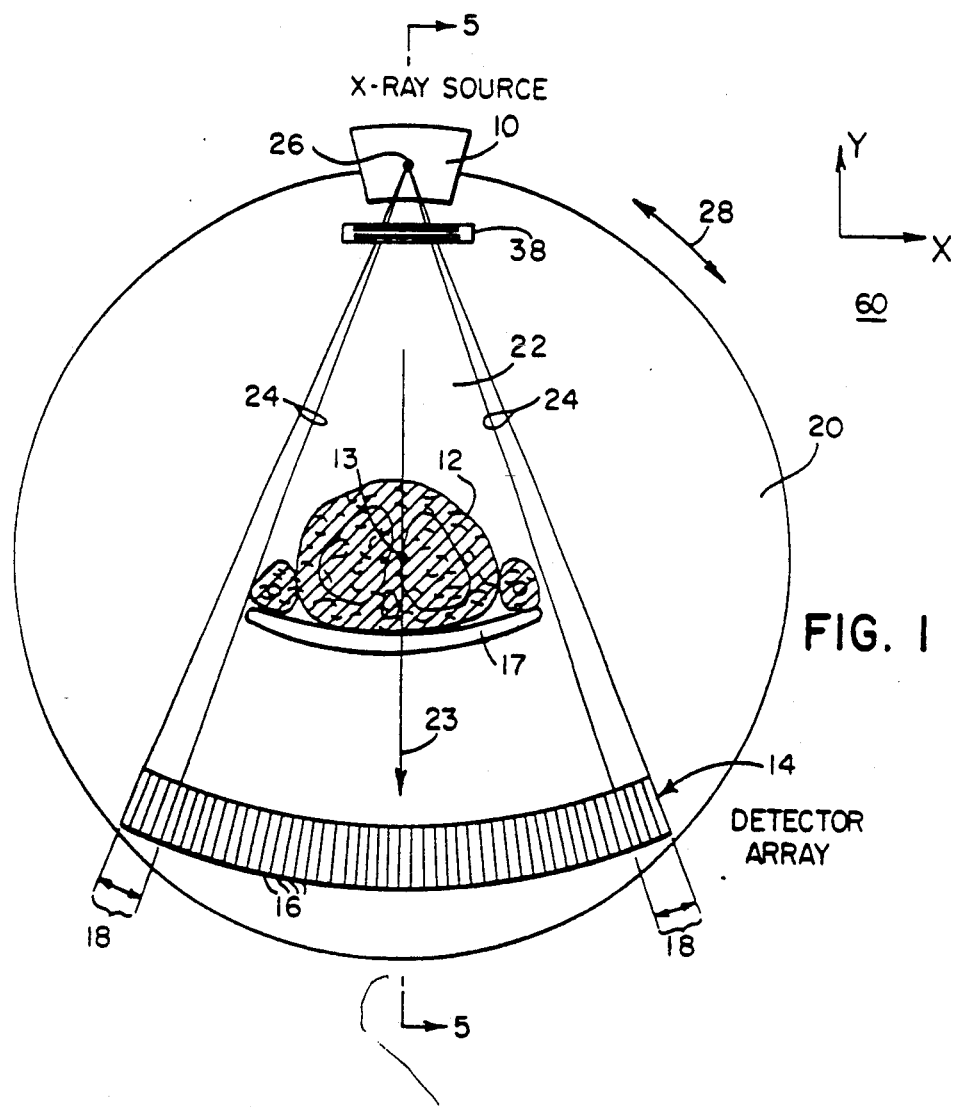
FIG. 1 is a schematic representation CT system gantry including an x-ray source and x-ray detector as may be used with the present invention.

Referring to FIG. 1, a gantry 20, such as may be used in a "third generation" computed tomography (CT) scanner, includes an x-ray source 10 collimated by collimator 38 to project a fan beam of x-rays 22 through imaged object 12 to detector array 14. The x-ray source 10 and detector array 14 rotate on the gantry 20 about center of rotation 13. The rotation of the gantry 20, as indicated by arrow 28 is within a gantry plane 60, aligned with the x-y plane of a Cartesian coordinate system.

The imaged object 12 rests on table 17 which is radiotranslucent so as not to interfere with the imaging process. Table 17 may be controlled so that its upper surface translates along the z axis perpendicular to the x-y imaging plane, moving the imaged object 12 across the gantry plane 60.

The detector array 14 is comprised of a number of detector elements 16, organized within the gantry plane 60, which together detect the projected image produced by the attenuated transmission of x-rays through the imaged object 12.

The fan beam 22 emanates from a focal point 26 in the x-ray source 10 and is directed along a fan beam axis 23 centered within the fan beam 22. The fan beam angle, measured along the broad face of the fan beam, is larger than the angle subtended by the imaged object 12 so that two peripheral beams 24 of the fan beam 22 are transmitted past the body without substantial attenuation. These peripheral beams 24 are received by peripheral detector elements 18 within the detector array 14.

Figure 6:
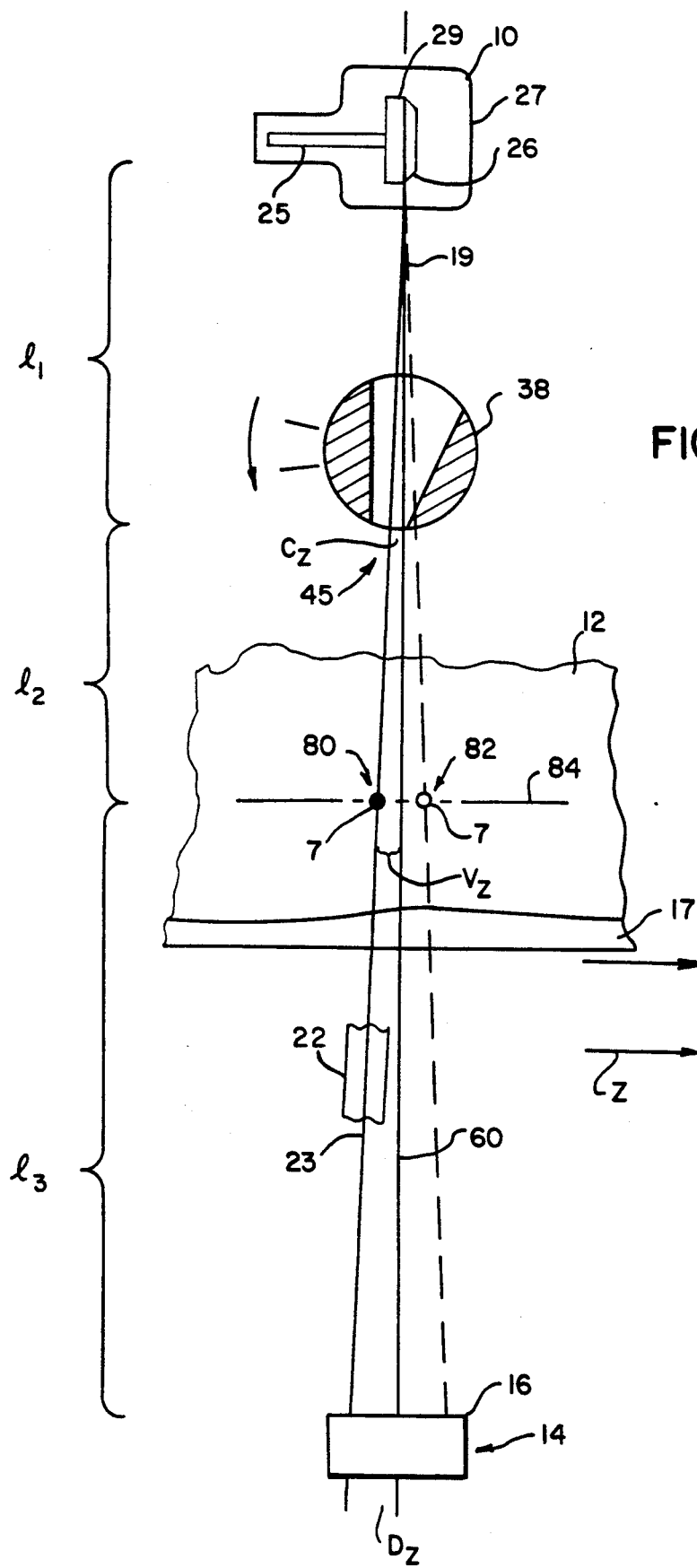
FIG. 6 is a cross-sectional view of the path of the x-ray fan beam, taken along line 5—5 in FIG. 1, with the x-ray tube anode, the collimator and the detector array exaggerated for clarity and showing a first method of reducing helix offset requiring only movement of the collimator.

Referring to FIG. 6, the x-ray source 10 includes an anode 29 position within an evacuated glass envelope and rotated about anode shaft 25 for heat dispersion. A stream of electrons from a cathode (not shown) is accelerated against the face of the anode 29 to produce the x-ray beam 19. The face of the anode 29 is beveled with respect to the fan beam axis 23 so that radial displacement of the electron beam by focussing plates, (not shown) as is known in the art, will produce a z-axis displacement of the focal point 26. The amount of this displacement may be controlled by x-ray controller 62.

Figure 2:
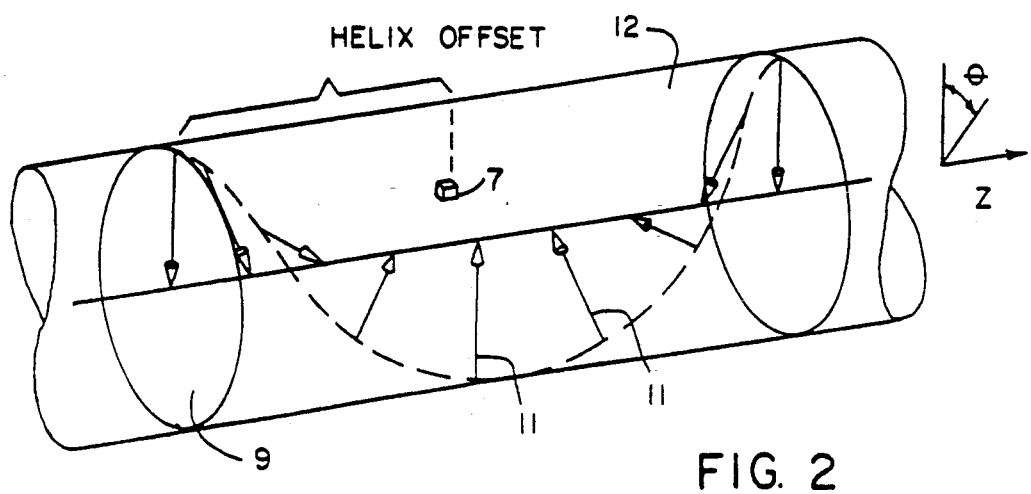
FIG. 2 is a schematic illustration of the imaged object of FIG. 1 showing the relative orientation of the gantry and gantry axis with respect to the imaged object for helical scanning. The pitch of the helical scanning is exaggerated for clarity.

Referring to FIG. 2, the angular position θ of the gantry 20 along the z-axis with respect to the imaged object 12 is shown by arrows 11. The z-axis position of the imaged object 12 with respect to the gantry plane 60 changes constantly during the acquisition of each tomographic projection set. Accordingly, arrows 11 are shifted along a helix within the imaged object 12 along the z-axis. The pitch of the helix will be referred to as the scanning pitch. The z-axis distance from the center 9 of the slice being acquired to the volume elements 7 intercepting the fan beam 22 is termed the "helix offset" of that volume element. In the present invention the fan beam axis 23 may be shifted along the z-axis during the helical scan to reduce the helix offset as will be described.

Referring to FIG. 3, uncollimated x-rays 19 radiating from the focal point 26 in the x-ray source 10 (not shown in FIG. 3) are formed into a coarse fan beam 21 by primary aperture 40. As is understood in the art, the uncollimated x-rays 19 are produced by a high voltage x-ray tube typically including a rotating anode (not shown) receiving a high energy beam of electrons and re-emitting x-ray radiation. The coarse fan beam 21 is collimated into fan beam 22 by means of collimator 38.

Referring generally to FIGS. 3, 4(a) and 4(b), collimator 38 is comprised of a cylindrical x-ray absorbing molybdenum mandrel 39 held within the coarse fan beam 21 on bearings 42 allowing the mandrel 39 to rotate along its axis. A plurality of tapered slots 41 are cut through the mandrel's diameter and extend along the length of the mandrel 39. The slots 41 are cut at varying angles about the mandrel's axis to permit rotation of the mandrel 39 to bring one such slot 41 into alignment with the coarse fan beam 21 so as to permit the passage of some rays of the coarse fan beam 21 through the slot 41 to form fan beam 22.

Referring to FIG. 4(a) and 4(b), the tapered slots 41 are of varying width and hence the rotation of the mandrel 39 allows the width of the fan beam 22 to be varied between narrow (1 mm) as shown in FIG. 4(b) and wide (10 mm) as shown in FIG. 4(b). The slots 41 ensure dimensional accuracy and repeatability of the fan beam 22.

The slots 41 are tapered so that the entrance aperture 43 of each slot 41, when orientated with respect to the coarse fan beam 21, is wider than the exit aperture 45. The exit aperture 45 defines the width of the fan beam 22 and the extra width of the entrance aperture 43 prevents either edge of the entrance aperture 43 from blocking the coarse fan beam 21 during small angular rotation of the mandrel 39. Such small rotations of the mandrel 39 are used to provide adjustment of the z-axis position of the fan beam 22 as will be discused in detail below.

Referring again to FIG. 3, a positioning motor 48 is connected to one end of the mandrel 39 by flexible coupling 50. The other end of the mandrel 39 is attached to a position encoder 46 which allows accurate positioning of the mandrel by motor 48. Fan beam angle shutters 44 at either ends of the mandrel 39 control the fan beam angle.

Figure 5:
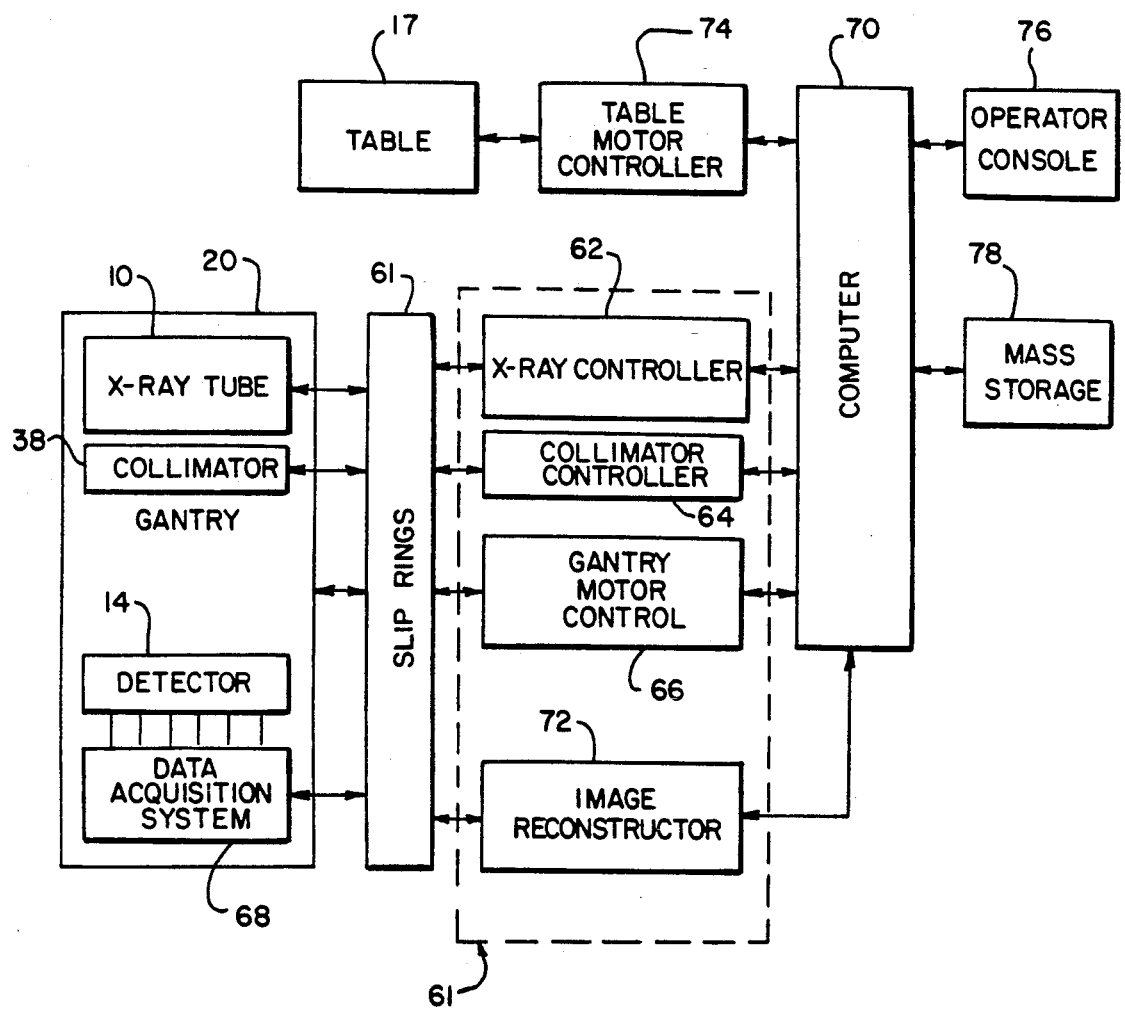
FIG. 5 is a block diagram showing the control system for the collimator and x-ray focal point of FIG. 3 according to the present invention.

Referring now to FIG. 5, the control system of a CT scanner, suitable for use with the present invention, has gantry associated control modules 61 which include: x-ray controller 62 which provides power and timing signals to the x-ray source 10, and which in certain embodiments of the invention, controls the position of the focal point 26; collimator controller 64 which controls the rotation of the collimator 38; gantry motor controller 66 which controls the rotational speed and position of the gantry 20; and the data acquisition system 68 which receives projection data from the detector array 14 and converts the data to digital words for later computer processing.

The gantry associated control modules 61 communicate with the x-ray source 10, collimator 38 and detector 14 via slip rings 61. It will be recognized that direct cabling using a take up reel may be substituted for the slip rings 61 for a limited gantry rotation system.

The x-ray controller 62, the collimator controller 64 and the gantry motor 66 controller are connected to a computer 70. The computer 70 is a general purpose minicomputer such as the Data General Eclipse MV/7800C and may be programmed to synchronize the rotation of the gantry 20 with the position of the fan beam 22 per the present invention as will be described in detail below.

The data acquisition system 68 is connected to image reconstructor 72 which receives sampled and digitized signals from the detector array 14 via the data acquisition system 68 to perform high speed image reconstruction according to methods known in the art. The image reconstructor 72 may be an array processor such as is manufactured by Star Technologies of Virginia.

The speed and position of table 17 along the z-axis is communicated to and controlled by computer 70 through of table motor controller 74. The computer 70 receives commands and scanning parameters via operator console 76 which is generally a CRT display and keyboard which allows an operator to enter parameters for the scan and to display the reconstructed image and other information from the computer 70. A mass storage device 78 provides a means for storing operating programs for the CT imaging system, as well as image data for future reference by the operator.

Referring now to FIG. 6, the z-axis position of the exit aperture 45 of the collimator 38 may be adjusted so that the fan beam 22, as indicated by fan beam axis 23, diverges from the gantry plane 60 in the z-axis dimension during the acquisition of the first projection of a projection set. The amount of divergence of the fan beam axis 23 from the gantry plane 60 is such that a volume element 7 at position 80 within a slice and moving toward the gantry plane 60 with motion of table 17, is intersected by the fan beam axis 23.

The position of the table 17 during the acquisition of the projection set is determined by the table motor controller 74. The collimator 38 as controlled by the collimator controller 64 is coordinated by computer 70 with the position of table 17 so that during the movement of the table 17 and imaged object 12, the fan beam axis 23 is swept as to constantly intercept volume element 7.

As the projections of each projection set are acquired, during a period $T_1$, the imaged object 12 is translated along the z-axis with respect to the gantry plane 60 so that volume element 7 ultimately moves to position 82 at the last projection of the projection set. Typically, the amount of translation will be equal to the slice thickness w.

At the completion of the acquisition of the projection set, the exit aperture 45 of the collimator 38 is returned to the position it had at the start of the projection set, moving in the opposite direction, during a period $t_2$, so that the fan beam axis 23 intercepts a new volume element in a new slice. The new volume element has the same relative position 80 with respect to the gantry plane 60 as did volume element 7 at the start of the acquisition of the previous projection set. Preferably, positions 80 and 82 are located symmetrically about the gantry plane 60 so as to reduce the maximum deviation of the fan beam axis 23 from the gantry plane 60 during any acquisition.

At the halfway point in the acquisition of the projection set, the focal point 26, the center line of the exit aperture 45 of the collimator 38, fan beam axis 23 and the center of illumination of the detector array 14 will be perfectly aligned with the gantry plane 60. At all other times, these various points may deviate from the gantry plane 60. The measures of the deviation of the center line of the exit aperture 45 of the collimator 38, the point of intersection of the fan beam axis 23 with the translation axis 84 of the imaged object 12, and the center of illumination of the detector array 14 from the gantry plane will be termed $C_z$, $V_z$, and $D_z$ respectively. Although the position of the fan beam axis 23 is employed as a point of reference, it should be remembered that the fan beam 22 extends for a finite distance on either side of the axis 23 and it is the entirety of the fan beam 22 which must be intercepted by the face of the detector element 16.

For the first described embodiment shown in FIG. 6, $F_z$, the position of the focal point 26 with respect to the gantry plane 60 is constant and zero.

Figure 10:
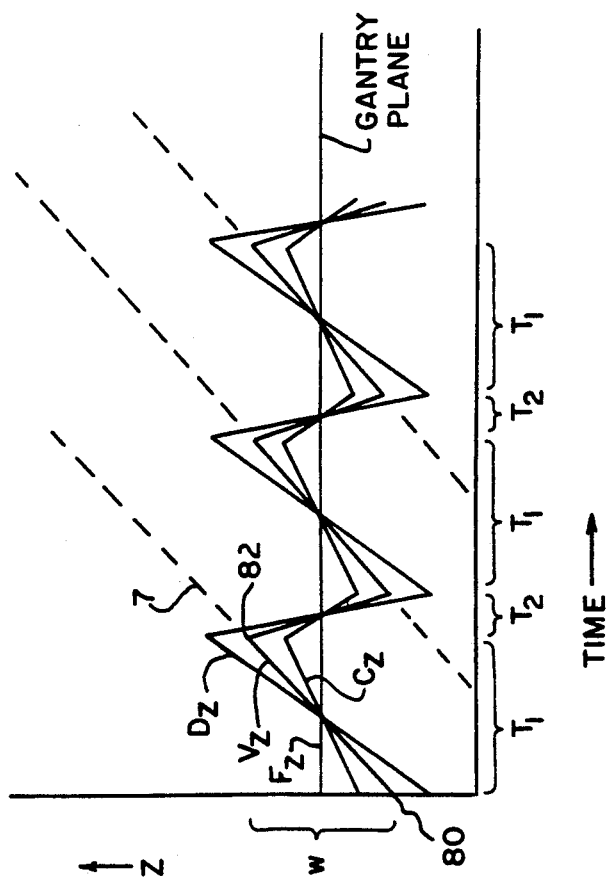
FIG. 10 is graph of the z-axis displacement with time for the collimator, the illumination area of the detector and the imaged element volume for the method of FIG. 6.

Referring to FIG. 10, during the first period $T_1$ of the acquisition of a projection set, the displacement of the collimator $C_z$ will increase so that the fan beam axis 23 tracks the movement of the volume element 7. For large values of $l_2$ and $l_3$ and small values of slice thickness w, the relationship between the collimator displacement $C_z$ and the displacement $V_z$ of the fan beam axis 23 with axis of translation 84 of the volume element 7 is:

$$C_z = V_z \frac{l_1}{l_1 + l_2} \quad (1)$$

where $l_1$ is the distance between the focal point 26 and the exit aperture 45 of the collimator 38 and $l_2$ is the distance between the exit aperture 45 and the translation axis 84 of the volume element 7. Accordingly, during the first period $T_1$, the position of table 17 as determined via the table motor controller 74, determines the position of the exit aperture 45 after suitable scaling by computer 70 as given in equation (1) above.

During a second time period $T_2$, being as little as 20 milliseconds after the first time period $T_1$, the exit aperture 45 is returned to the position it had at the start of that acquisition of projections to prepare for acquisition of a second projection set. Preferably this period $T_2$ is made a short as possible by moving the collimator 38 at its maximum speed. During this return period $T_2$, no projection data is taken and the x-ray fan beam 22 may be decreased in intensity according to any of several methods known in the art such as decreasing current flow to the x-ray tube or shuttering the x-ray beam 19.

It will be noted that the displacement $D_z$ of the fan beam axis 23 with respect to the surface of the detector array 14 will be larger than the displacement $V_z$ according to the following ratio:

$$D_z = V_z \frac{l_1 + l_2 + l_3}{l_1 + l_2} \quad (2)$$

where $l_3$ is the distance between the axis of translation 84 of the volume element 7 and the exposed surface of detector array 14. Generally, the detector elements 16 of detector array 14 exhibit a change of sensitivity as a function of the z-axis position of their illumination. Hence a variation in $D_z$ will introduce some variation into the projections measurements. This variation may be corrected by using the peripheral beams 24 and peripheral detector elements 18 to provide a reference for correcting sensitivity variation according to compensation methods understood in the art. One such method is given in U.S. Pat. No. 4,559,639 hereby incorporated by reference.

Figure 7:
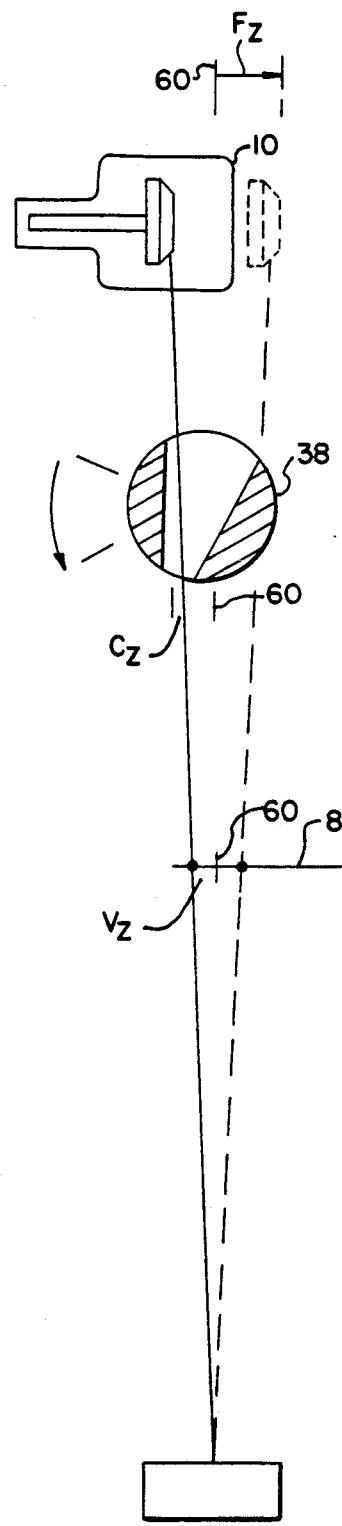
FIG. 7 is a cross-sectional view, similar to that of FIG. 6, of a second method of reducing helix offset requiring movement of the collimator and the x-ray focal point but reducing movement of the illuminated area of the detector.
Figure 11:
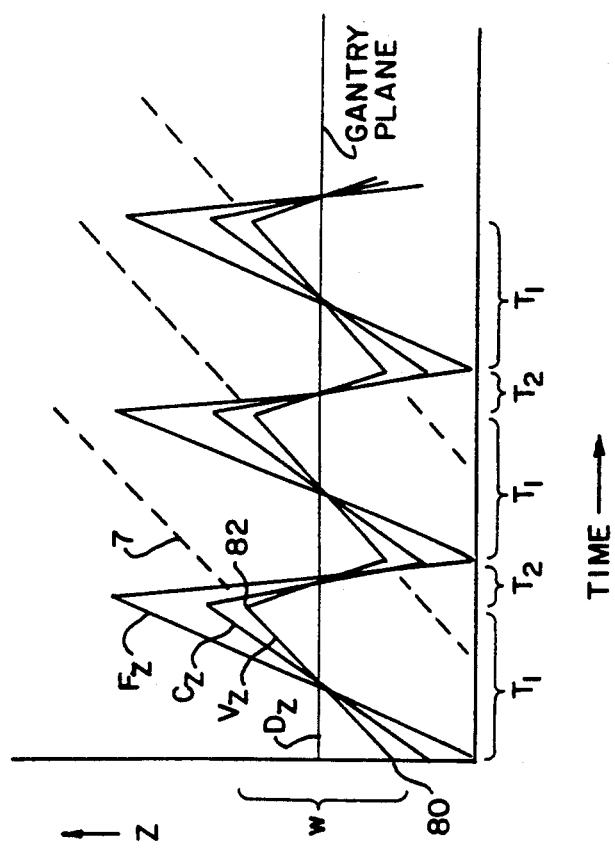
FIG. 11 is graph of the z-axis displacement with time for the collimator, the illumination area of the detector and the imaged element volume for the method of FIG. 7.

In a second embodiment shown in FIGS. 7 and 11, both the x-ray focal point 26 and the exit aperture 45 of the collimator 38 are moved. Movement of the x-ray focal point 26 is accomplished by refocussing the electron beam on the anode 29 as has been previously described or by physical translation of the x-ray source 10 under the control of servo motors or through the use of magnetic bearings. The measure of the deviation of the focal point 26 from the gantry plane 60 will be termed: $F_z$. Referring to FIG. 11, in this second embodiment, the intersection $D_z$ of the fan beam axis 23 on the detector array 14 is maintained constant (at zero displacement) by controlling the displacement $F_z$ of the focal point and the displacement $C_z$ of the exit aperture 45 with respect to the displacement $V_z$ of the volume element as follows:

$$F_z = V_z \frac{l_1 + l_2 + l_3}{l_3} \quad (3)$$

and $$C_z = V_z \frac{l_2 + l_3}{l_3} \quad (4)$$

Figure 14:
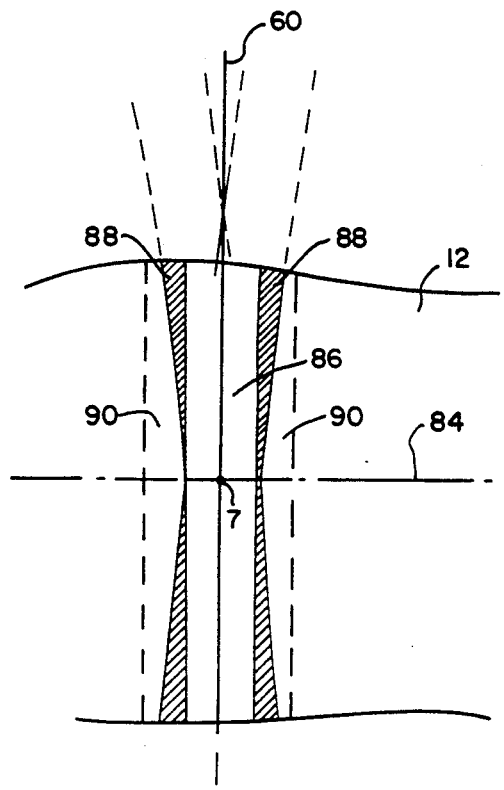
FIG. 14 is an exaggerated cross-sectional view of the imaged object taken along 5—5 in FIG. 1, showing a single slice thickness, the effective thickness for helical scanning and for helical scanning with reduced helix offset per the methods of FIGS. 6-8.
Figure 15:
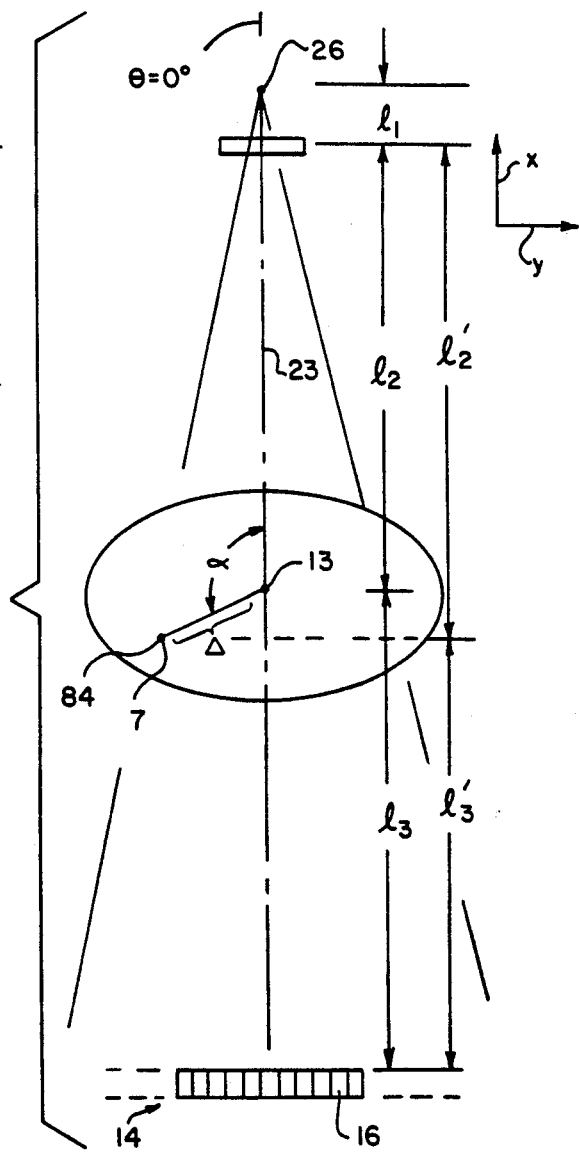
FIG. 15 is a schematic representation similar to FIG. 1 showing the determination of $l'_1$ and $l'_2$ for offset translation axes.

Referring to FIG. 14, the acquisition volume 86 within the imaged object 12 over which projection data is acquired in a non-helical scan will be approximately one half of acquisition volume of a helical scan: assuming that the scanning pitch times the rotation for one projection set is approximately equal to the slice thickness w. The present invention, as described in the above two embodiments, enlarges the acquisition volume over the non-helical acquisition volume 86 by flanking volumes 88 which are outwardly conically concave. This increase in acquisition volume represented by volumes 88 increases the helix offset of the projection data slightly but much less than that produced by helical scanning which adds areas 90 to effectively double the acquisition volume. In general, the greater the distance $l_1 + l_2$ in comparison to the radius of the image object 12 about the translation axis 84, the less the flanking volume 88 and thus the less the helix offset of the data.

Figure 8:
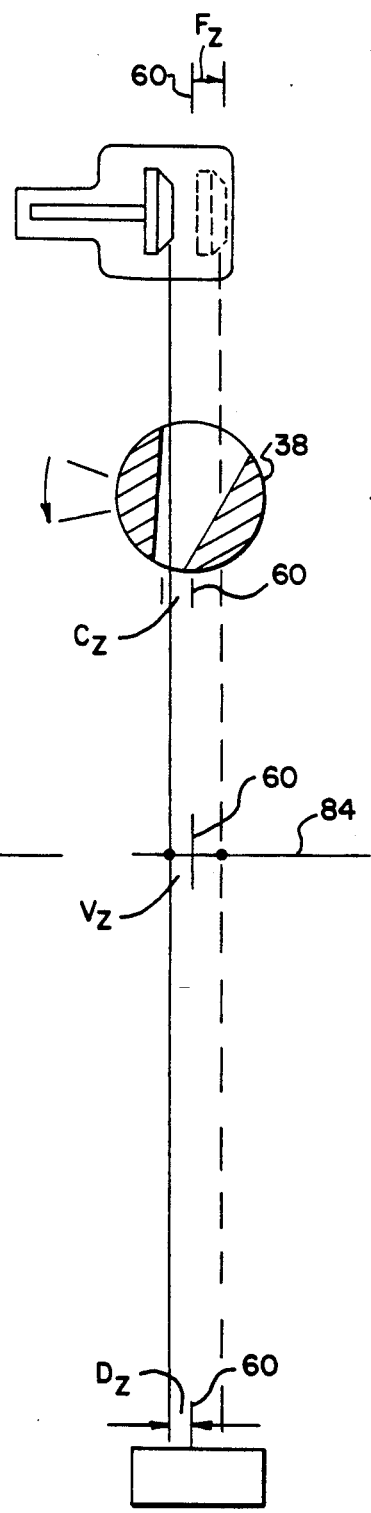
FIG. 8 is a cross-sectional view, similar to that of FIG. 6, a third method of reducing helix offset requiring movement of the collimator and the x-ray focal point but further reducing skew error.
Figure 12:
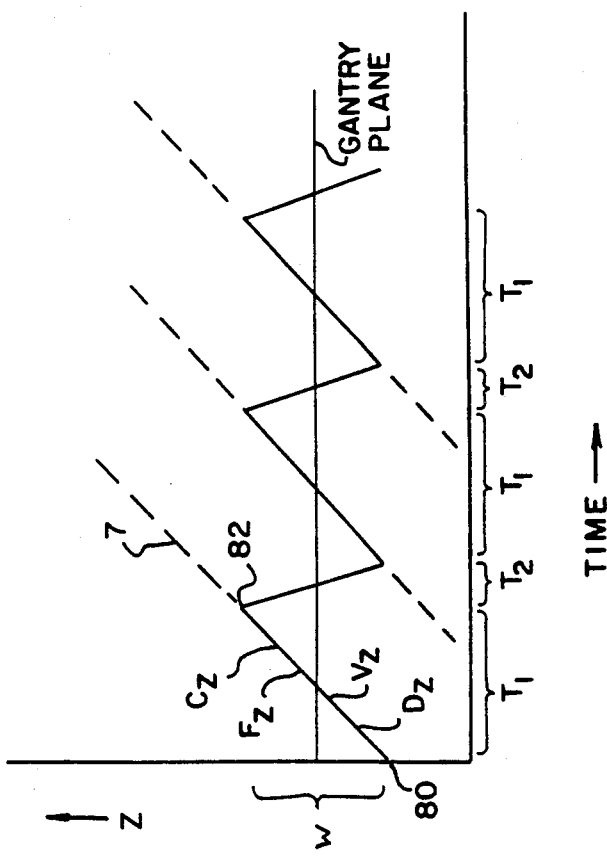
FIG. 12 is graph of the z-axis displacement with time for the collimator, the illumination area of the detector and the imaged element volume for the method of FIG. 8.

Referring to FIGS. 8 and 14, a third embodiment of the invention eliminates the flanking volumes 88 and produces an acquisition volume 86 identical to that of non-helical 25 scanning. Referring to FIG. 12, the displacement $D_z$ of the collimator 38 and $F_z$ of the focal point 26 are set equal to the displacement $V_z$ of the volume element 7. The fan beam axis 23 is thus maintained parallel to the gantry plane 60 at all times.

Figure 9:
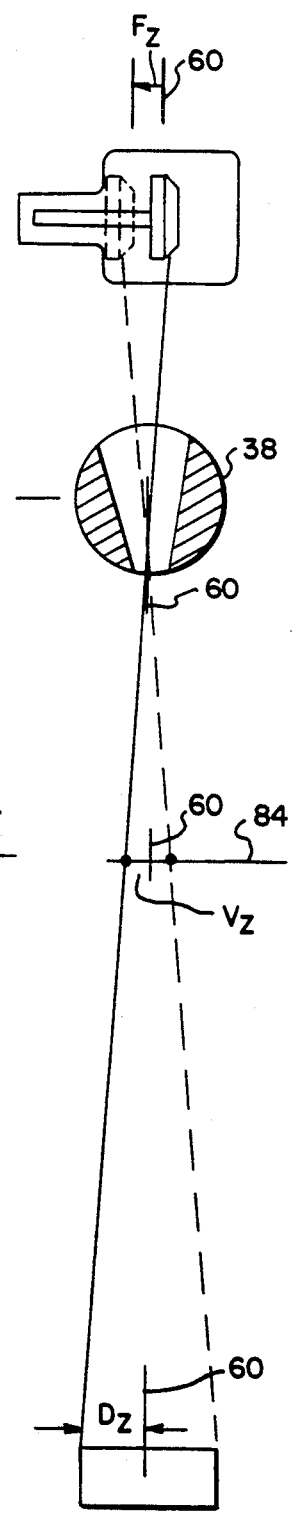
FIG. 9 is a cross sectional view, similar to that of FIG. 6, of a fourth method of reducing helix offset requiring only movement of the x-ray.
Figure 13:
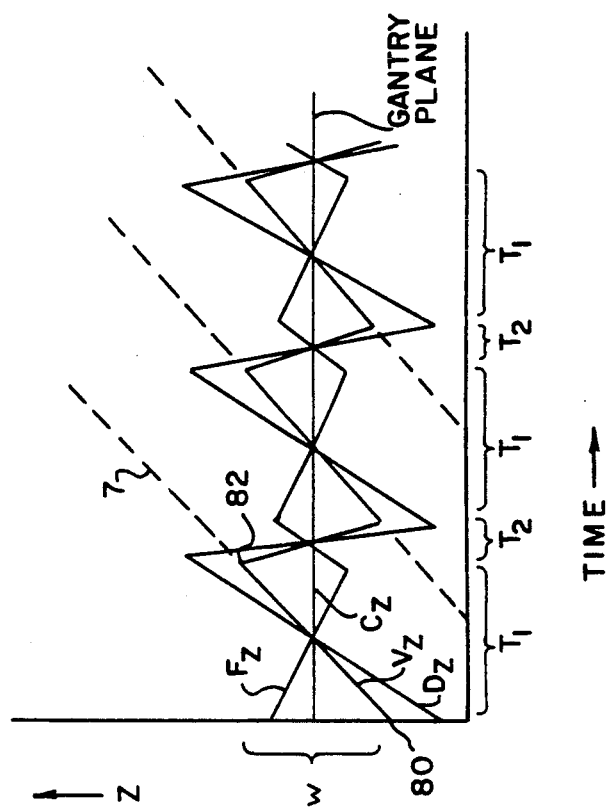
FIG. 13 is graph of the z-axis displacement with time for the collimator, the illumination area of the detector and the imaged element volume for the method of FIG. 9.

In a fourth embodiment, shown in FIGS. 9 and 13, the displacement $C_z$ of the exit aperture 45 of the collimator 38 is fixed (and equal to zero) and the displacement $F_z$ of the focal point 26 is adjusted according to the following relationship:

$$F_z = -V_z \frac{l_1}{l_2} \quad (5)$$

The acquisition volume (not shown) for this method and the amount of displacement $D_z$ of the fan beam axis 23 on the detector array 14 will be greater than the comparable quantities for the previously described method, for CT systems of similar dimensions as a result of the greater angular divergence of the fan beam axis 23 from the gantry plane 60 necessary to track a given volume element 7 without movement of the collimator 38.

For each of the above embodiments, the projection data for volume elements near volume element 7 on the translation axis 84, there will be little helix offset. To the contrary, the volume elements removed from volume element 7 and the translation axis 84 will have increasing amounts of helix offset for greater values of x and y as dictated by the angle of the fan beam axis 23 with respect to the gantry plane 60. For this reason, it may be desirable to position the volume element 7 and the translation axis 84 near internal structures of interest within imaged object 12.

The translation axis 84 will normally intersect the center of rotation 13 of the gantry 20. The center of rotation 13 and the translation axis 84 may both be moved within the imaged object simply by adjusting the height of table 17. Alternatively, the translation axis 84 may be moved independently from the center of rotation 13 by adjusting the fan beam angle as a function of gantry rotation 28. This is most easily accomplished by modifying the apparent value of $l_2$ and $l_3$ used by computer 70 in the above embodiments as a function of gantry angle $\theta$ as follows:

$$l_{2'} = l_2 - \cos(\theta + \alpha)(\Delta) \qquad (6)$$

$$l_{3'} = l_3 + \cos(\theta + \alpha)(\Delta) \qquad (7)$$

where $\alpha$ is the angle with respect to the center of rotation 13 between the volume of interest and gantry angle $\theta = 0$, $\Delta$ is the distance between the volume of interest and the center of gantry rotation 13, and $l_{2'}$ and $l_{3'}$ are substituted into the above equations in place of $l_2$ and $l_3$ respectively.

For the embodiments shown in FIGS. 6, 7, and 9, it will be understood that the amount of helix offset, reduced as it is, also varies as a function of the order of the projection within the projection set. For example, when the starting and ending positions 80 and 82 of the volume of interest 7 are symmetrically displaced about the gantry plane 60, the centermost projections will have no helix offset and the starting and ending projections will have the most helix offset. For this reason, it is desirable to weight the projections so as to de-emphasize the starting and ending projections and to emphasize the centermost projections of the projection set. Such weighting systems are disclosed in co-pending application Ser. No. 07/440,531 entitled: "Method for Reducing Patient Translation Artifacts in Tomographic Imaging" filed Nov. 22, 1989.

Finally, for the first, third, and forth embodiments, where the center of illumination of the detector 14 changes during the acquisition of projections, it is important that the detector 14 be sufficiently wide so as to always receive the entire fan beam 22 not just the fan beam axis 23.

In each of the first, third, and fourth embodiments, there is a practical limit as to how far the fan beam 22 may be swept. For helical scanning with a large pitch, corresponding to a large slice thickness w, the constraints of the physical mechanism employed to sweep the fan beam 22 may prevent the fan beam from tracking a particular volume element 7 during the acquisition of an entire projection set.

Figure 16:
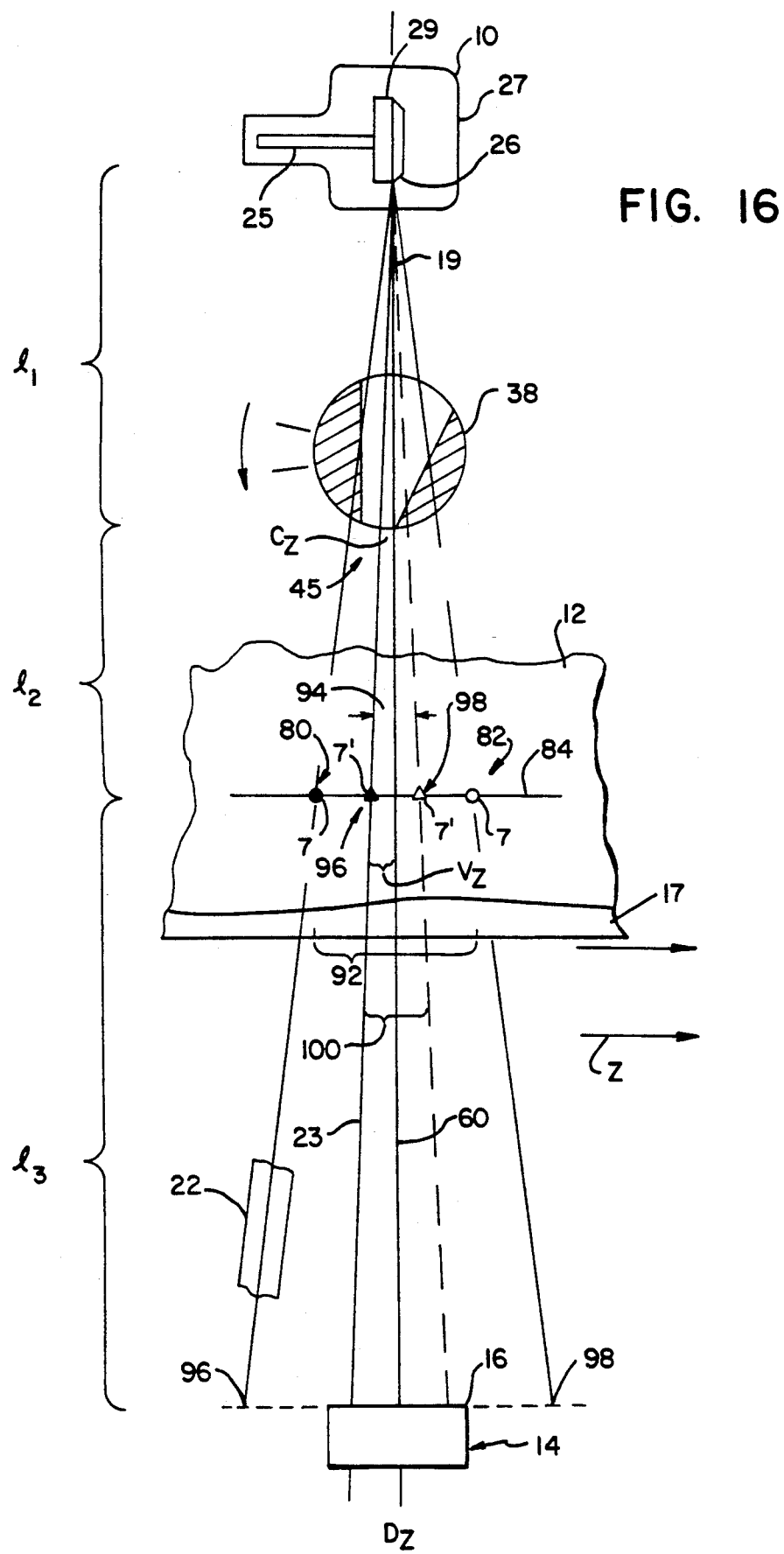
FIG. 16 is a cross-sectional view similar to FIG. 6 showing a situation where the translation of the imaged object during the acquisition of a projection set exceeds the compliance distance over which the fan beam may be swept.

Referring to FIG. 16, during a given acquisition of a projection set, a volume element 7 may move from position 80 to position 82 along the translation axis 84 by a translation distance 92. The translation distance 92 is generally equal to the slice thickness w. For thick slices, the translation distance 92 will be greater than the distance that the fan beam 22 may move along the gantry axis 84, between positions 96 and 98 as determined by a maximum sweep angle 94.

The maximum sweep angle 94 for the first, third and fourth embodiments can be dictated by the width of the detector array 14; sweep angles beyond the maximum sweep angle 94 would cause some portion of the fan beam 22 (not simply the fan beam axis 23) to move off the surface of the detector array 14 causing impermissible wasted irradiation of the patient. A maximum sweep angle 94 can also exist for the second embodiment of FIG. 7 as a result of physical constraints on the movement of the focal point 26 and collimator 38. The maximum sweep angle may be further limited to avoid use of the edges of the detector elements 14 along the z-axis, such edges frequently having non-linear responses, difficult to accurately characterize.

The maximum sweep angle 94 defines a compliance distance 100 along the translation axis 84. The compliance distance 100 is the distance separating position 96, at the intersection of the fan beam axis 23 and the translation axis 84 at one extreme of the maximum sweep angle 94, and position 98, at the intersection of the fan beam axis 23 and the translation axis 84 at the opposite extreme of the maximum sweep angle 94. For large slice thickness w, the compliance distance 100 will be significantly less than the translation distance 92.

Movement of the fan beam 22 beyond the surface of the detector array 14 for large translation distances 92 associated with large slice thicknesses w is unacceptable because it would needlessly expose the patient to ionizing radiation that does not contributing to the generation of an intensity signal.

Figure 17:
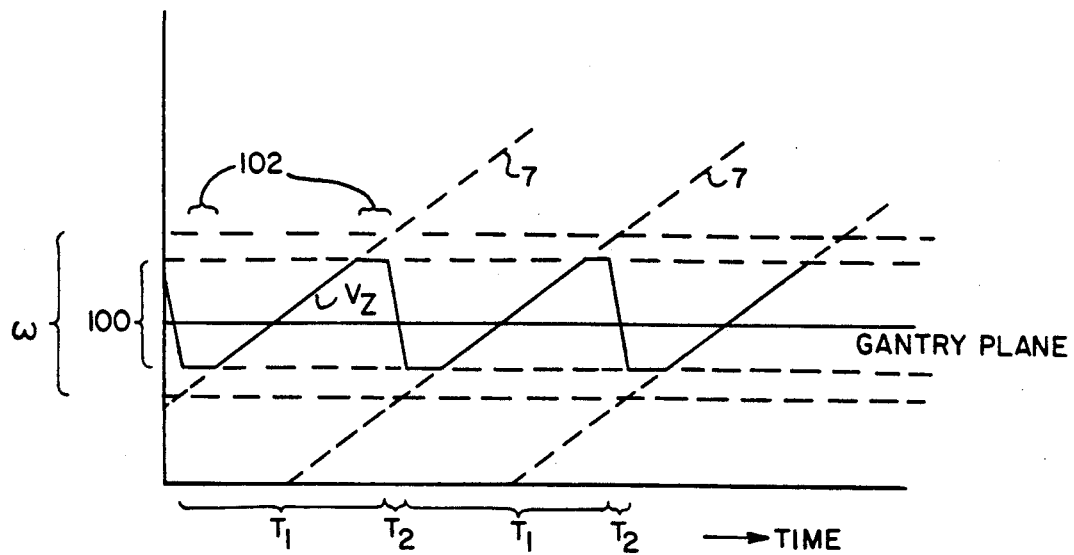
FIG. 17 is a graph of z-axis displacement of the fan beam with time showing a first method of reducing image artifacts produced in the situation shown in FIG. 16.

Referring now to FIG. 17, the sweeping of the fan beam 22 may be employed with large slice thicknesses by stopping the sweeping of the fan beam 22 at the limits of the compliance distance 100. In this case, the deviation of the
fan beam axis 23 at the translation axis, that is, $V_z$, is constrained to lie within the compliance distance 100.

Accordingly, in the embodiment of FIG. 17, motion of the fan beam 22 during $T_1$, as measured by $V_z$, is stopped at the limits 96 and 98 of the compliance distance 100. The periods of time 102 during which motion of the fan beam 22 ceases with respect to the gantry plane 60, are timed to occur symmetrically at either extreme of period $T_1$.

As before, during periods $T_2$ the fan beam 22 is rapidly swept back to its starting point 96 from its ending point 98.

It has been determined that even when the fan beam 22 is prevented from sweeping outside of the compliance distance 100 skew errors are significantly reduced. Additional improvement, however, may be obtained if the sweeping of the fan beam 22 is subject to two conditions. The first condition, as before, is that the fan beam be constrained to sweep only within the limits 96 and 98 of the compliance distance 100. The second condition is that abrupt changes in speed of sweeping of the fan beam 22 are eliminated. Apparently, constancy of sweeping speed is more important than the exact tracking of a volume element 7 by the fan beam 22.

Figure 18:
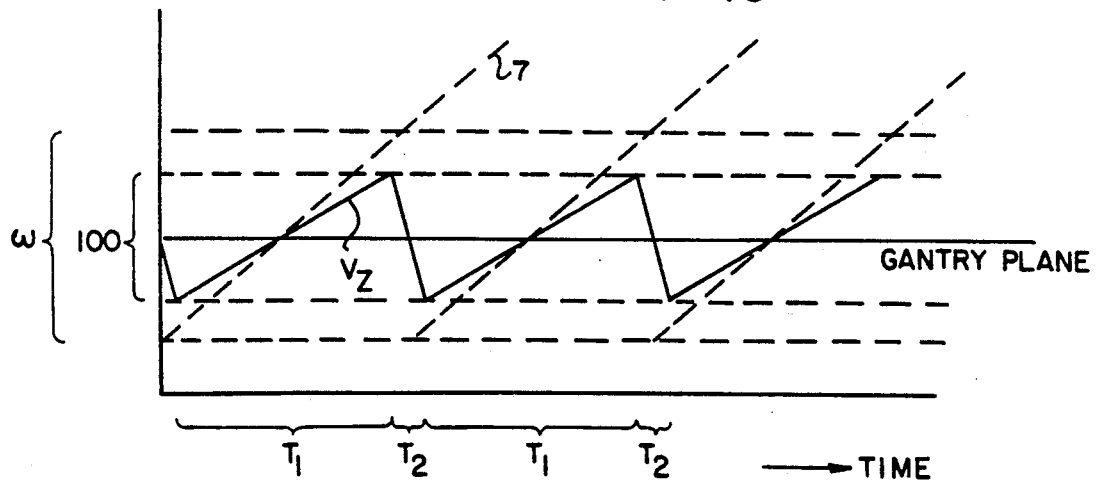
FIG. 18 is a graph of a z-axis displacement of the fan beam with time showing a second method of reducing image artifacts produced in the situation shown in FIG. 16.

Accordingly, in a further embodiment shown in FIG. 18, the fan beam 22 is controlled so as to sweep with essentially constant angular motion within the compliance distance 100 during period $T_1$. Because the volume element 7 moves by the larger translation distance w during that same period $T_1$, it will be apparent that the sweeping of the fan beam 22 does not track a particular volume element 7 but that during the helical scan, the volume element 7 catches up with the fan beam axis 23 and then passes the fan beam axis 23.

Although at present it is believed that constant angular sweeping of the fan beam 22 is preferred for reducing skew error within the constraints imposed by a compliance distance 100 smaller than the translation distance 92, this investigation suggests that other continuous functions of beam sweep angle and time may also realize an improvement in image artifacts over the embodiment of FIG. 17.

It will be apparent from an inspection of FIGS. 16 and 18 that the fan beam 22 will be centered on volume element 7 only at the mid-point of period $T_1$ where both the fan beam axis 23 and volume element 7 cross the gantry plane 60. It follows that the helix offset causing image artifacts in helical reconstruction is greatest for those projections obtained at the beginning and end of period $T_1$.

Accordingly, further improvements in image artifacts may be obtained by de-weighting those projections taken at the beginnings and ends of period $T_1$ as have been disclosed in the previously cited co-pending application Ser. No. 07/440,531 entitled:"Method for Reducing Patient Translation Artifacts in Tomographic Imaging" filed Nov. 22, 1989.

Many modifications and variations of the preferred embodiment which will still be within the spirit and scope of the invention will be apparent to those with ordinary skill in the art. For example, the collimator may be of a conventional bladed design. Further it will be apparent that this method is applicable to so called "fourth generation" CT machines where the detector array 14 is stationary and may surround the imaged object 12. Clearly the x-ray tube and collimator may be also mechanically translated and tipped as a single unit. Finally, the table motion need not be constant during the acquisition of successive projection sets but may be slowed, for example, during the period $T_2$ when the fan beam 22 repositions itself at a starting position. In order to apprise the public of the various embodiments that may fall within the scope of the invention, the following claims are made:

We claim:

1. An apparatus for acquiring a tomographic projection set of an imaged object, the apparatus comprising:
   an x-ray generator for projecting a beam of x-rays through the imaged object at a plurality of angles about the imaged object gantry plane substantially perpendicular to a translation axis;
   an x-ray detector opposing the x-ray generator through the imaged object for receiving the x-ray beam at the plurality of angles to create a projection set;
   a table for supporting and translating the imaged object by a translation distance along a translation axis with the acquisition of the projection set during a first period, the translation being concurrent with the projections of the plurality of angles;
   a means for alternately sweeping the beam by a predetermined compliance distance along the translation axis in a first direction during the first period, and in a second direction along the translation axis but counter to the translation of the imaged object during a second period, wherein the compliance distance is limited to less than the translation distance and wherein the beam of x-rays is received by the x-ray detector throughout the sweeping of the beam by the compliance distance.

2. The apparatus as recited in claim 1 including additionally an exposure controller for controlling the exposure of the imaged object by the x-ray beam during the first period so that the exposure during the first period is greater than the x-ray exposure of the imaged object by the x-ray beam during a second period.

3. The apparatus as recited in claim 2 wherein the exposure controller reduces the intensity of the x-ray beam during the second period.

4. The apparatus as recited in claim 1 wherein the means for alternatively sweeping sweeps the x-ray beam during a first portion of the first period so as to maintain the beam centered on a predetermined volume element on the translation axis in the imaged object within the predetermined compliance distance and stops the sweeping of the x-ray beam during a second portion of the first period at the limit of the predetermined compliance distance.

5. The apparatus as recited in claim 4 wherein the first portion is divided equally between the start and end of the first period.

6. The apparatus as recited in claim 1 wherein the means for alternatively sweeping, sweeps of the x-ray beam during the first period so as to maintain a constant angular motion of the beam during the first period.

7. The apparatus recited in claim 1 wherein the means for alternatively sweeping comprises a collimator positioned between the x-ray generator and the imaged object, the collimator having an aperture movable along the translation axis.

8. The apparatus recited in claim 1 wherein the means for alternatively sweeping comprises an x-ray source having a focal point movable along the translation axis and collimator having a aperture movable along the translation axis.

* * * * *